US006900299B1

(12) United States Patent
Mohapatra et al.

(10) Patent No.: US 6,900,299 B1
(45) Date of Patent: May 31, 2005

(54) INTERRUPTING THE INTERACTION OF INTERCELLULAR ADHESION MOLECULE-1 AND RESPIRATORY SYNCYTIAL VIRUS FOR PREVENTION AND TREATMENT OF INFECTION

(75) Inventors: Shyam S. Mohapatra, Tampa, FL (US); Aruna Behera, Tampa, FL (US); Hiroto Matsuse, Nagasaki (JP); Mukesh Kumar, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 10/440,000

(22) Filed: May 16, 2003

Related U.S. Application Data (63) Continuation of application No. 09/523,054, filed on Mar. 10, 2000, now abandoned.
(60) Provisional application No. 60/123,999, filed on Mar. 11, 1999.

(51) Int. Cl.$^7$ ............................................... C07H 21/02
(52) U.S. Cl. ................ 536/22.1; 424/143.1; 424/278.1; 424/178.1; 436/6; 514/44; 536/23.1; 530/387.1
(58) Field of Search ........................... 514/44; 536/23.1, 536/22.1; 530/387.1; 436/6; 424/178.1, 278.1, 143.1

(56) References Cited

PUBLICATIONS

Kumasaka et al., J. Clin. Invest. 97:2362–2369, 1996.*
Sly, P.D. and M.E. Hibbrt "Childhood asthma following hospitalization with acute viral bronchiolitis in infancy" *Pediatr. Pulmonol.*, 1989, 7:153–158.
Staunton, D.E. et al. "Internalization of a major group human rhinovirus does not require cytoplasmic or transmembrane domains of ICAM-1"*J. Immunol.*, 1992, 148:3271–3274.
Staunton, D.E. et al. "A cell adhesion molecule, ICAM-1, is the major surface receptor for rhinoviruses" *Cell*, 1989, 56:849–853.
Stott, E.J. et al. "Immune and histopathological responses in animals vaccinated with recombinant vaccinai viruses that express individual genes of human respiratory syncytial virus" *J. Virol.*, 1987, 61:3855–3861.
Taylor, G. et al. "Respiratory syncytial virus infection in mice" *Infection and Immunity*, 1984, 43:649–655.
Tomassini, J.E. et al. "cDNA cloning reveals that the major group rhinovirus receptor on HeLa cells is intercellular adhesion molecule 1" *Proc. Natl. Acad. Sci. USA*, 1989, 86:4907–4911.
Vignola, A.M. et al. "HLA–DR and ICAM–1 expression on bronchial epithelial cells in asthma and chronic bronchitis" *Am. Rev. Respir. Dis.*, 1993, 148:689–694.

Xu, H. et al. "Leukocytosis and resistance to septic shock in intercellular adhesion molecule 1–deficient mice" *J. Exp. Med.*, 1994, 180:95–109.
Hegele, R.G. et al. "Persistence of respiratory syncytial virus genome and protein after acute bronchiolitis in guinea pgis" *Chest*, 1994, 105:1848–1854.
Hus, S.C. et al. "Reduction of respiratory synchytial virus titer in the lungs of mice after intranasal immunization with a chimeric peptide consisting of a single CTL epitope linked to a fusion peptide" *Virology*, 1998, 240:376–381.
Huguenel, E.D. et al. "Prevention of rhinovirus infection in chimpanzees by soluble intercellular adhesion molecule–1" *Am. J. Respir. Crit. Care Med.*, 1997, 155:1206–1210.
Jeng, M.J. and Lemen, R.J. "Respiratory syncytial virus bronchiolitis" *Am Fam. Physician.*, 1997, 55:1139–1146.
Kelly, K.J. et al. "Intercellular adhesion molecule–1–deficient mice are protected against ischemic renal injury" *J. Clin. Invest.*, 1996, 97:1056–1063.
Kumasaka, T. et al. "Role of the intercellular adhesion molecule–1 (ICAM–1) in endotoxin–induce pneumonia evaluated using ICAM–1 antisense oligonucleotides, anti–I-CAM–1 monoclonal antibodies, and ICAM–1 mutant mice" *J. Clin. Invest.*, 1996, 97:2362–2369.
Levine, S. et al. "Demonstration that glycoprotein G is the attachment protein of respiratory syncytial virus" *J. Gen. Virol.*, 1987, 68:2551–2524.
Li, X. et al. "Protection against respiratory syncytial virus infection by DNA immunization" *J. Exp. Med.*, 1998, 188:681–688.
Makgoba, M.W. et al. "Functional evidence that intercellular adhesion molecule–1 (ICAM–1) is a ligand for LFA–1–dependent adhesion in T cell–mediated cytotoxicity" *Eur. J. Immunol.*, 1998, 18:637–640.

(Continued)

*Primary Examiner*—Laurie Scheiner
(74) *Attorney, Agent, or Firm*—Saliwanchik Lloyd & Saliwanchik (57) ABSTRACT

There is provided a method of preventing a respiratory infection by administering an effective amount of an agent for regulating ICAM-1 expression. Also provided is a composition for the prevention of respiratory infection including an agent which regulates ICAM expression. method of preventing RSV infection by administering an effective amount of an agent that interferes with the binding of RSV to ICAM-1. A method of preventing RSV infection by administering an effective amount of an agent that down regulates the expression of ICAM-1, thereby decreasing RSV binding to ICAM-1 is also provided. There is provided a method of treating RSV infection by administering an effective amount of an agent for down regulating ICAM-1 expression. A method of blocking RSV-ICAM-1 interaction by administering an effective amount of agents for blocking ICAM sites of binding is provided. Also provided is a compound for blocking RSV-ICAM-1 interaction including an agent for blocking ICAM sites of binding.

15 Claims, 4 Drawing Sheets

OTHER PUBLICATIONS

Olmsted, R.A. et al. "Expression of the F glycoprotein of respiratory syncytial virus by a recombinant vaccinia virus: Comparison of the individual contributions of the F and G glycoproteins to host immunity" *Proc. Natl. Acad. Sci. USA,* 1986, 83:7463–7466.

Openshaw, P.J.M. "Immunity and immunopathology to respiratory syncytial virus" *Am. J. Res. Crit. Care Med.,* 1995, 152:S59–S62.

Saito, T. et al. "Respiratory syncytial virus induces selective production of the chemokine RANTES by upper airway epithelial cells" *J. Infect. Dis.,* 1997, 175:497–504.

Sligh, J.E. et al. "Inflammatory and immune responses are impaired in mice deficient in intercellular adhesion molecule 1" *Proc. Natl. Acad. Sci USA,* 1993, 90:8529–8533.

Almenar–Queralt, A. et al. "Apical topography and modulation of ICAM–1 expression on activated endothelium" *Am. J. Pathol.,* 1995, 147:1278–1288.

Anderson, J.J. et al. "Analysis of the local and systemic immune responses induced in BALB/c mice by experimental respiratory syncytial virus infection" *J. Gen. Virol.,* 1990, 71:1561–1570.

Becker, S.W. et al. "RSV infection of human airway epithelial cells causes production of the β–chemokine RANTES" *Am. J. Physiol.* 1997, 272 (Lung Cell. Mol. Physiol. 16):L512–520.

Behera, A.K. et al. "Respiratory syncytial virus induces the expression of 5–lipoxygenase and endothelin–1 in bronchial epithelial cells" *Bichem. Biophys. Res. Commun.,* 1998, 251:704–709.

Bella, J. et al. "The structure of the two amino–terminal domains of human ICAM–1 suggests how it functions as a rhinovirus receptor and as an LFA–1 integrin ligand", *Proc. Natl. Acad. Sci. USA,* 1998, 95:4140–4145.

Casanovas, J.M. et al. "A dimeric crystal structure for the N–terminal two domains of intercellular adhesion molecule–1" *Proc. Natl. Acad. Sci. USA,* 1998, 95:4134–4139.

Center for Disease Control and Prevention, "Respiratory syncytial virus activity—United States, 1996–1997 season", *MMWR,* Dec. 6, 1996, 45(48):1053–1055.

Chini, B.A. et al. "Essential roles of NF–κB and C/EBP in the regulation of intercellular adhesion molecule–1 after respiratory syncytial virus infection of human respiratory epithelial cell cultures" *J. Virol.,* 1998, 72:1623–1626.

Collins, P.L. "The molecular biology of human respiratory syncytial virus (RSV) of the genus Pneumovirus" in The Paramyxoviruses. D.W. Kingsbury, Editor, Plenum, New York, 1991, Chapter 4, pp. 103–162.

Fixler, D.E. "Respiratory syncytial virus infection in children with congenital heart disease: A review" *Ped. Cardiol.,* 1996, 17:163–168.

Graham, B.S. "Pathogenesis of respiratory syncytial virus" *Am. J. Respir. Crit. Care Med.,* 1995, 152:S63–S66.

Graham, B.S. et al. "Primary respiratory syncytial virus infection in mice" *J. Med. Virol.,* 1988, 26:153–162.

Greve, J.M. et al. "The major human rhinovirus receptor is ICAM–1" *Cell,* 1989, 56:839–847.

Armstrong, D.S. and S. Menahem "Cardiac arrythmias as manifestation of acquired heart disease in association with pediatric respiratory syncytial virus infection" *J. Ped. Child Health,* 1993, 29:309–311.

Arnold, R.H. et al. "Expression of adhesion molecules (ICAM–1, LFA–3) on human epithelial cells (A549) after respiratory syncytial virus infection" *Int. Arch Allergy Immunol.,* 1995, 107:392–393.

Becker, S. et al. "Interleukin–8 expression in normal nasal epithelium and its modulation by infection with respiratory syncytial virus and cytokines tumor necrosis factor, interleukin–1 and interleukin–1 and interleukin–6" *Am. J. Respir. Cell Mol. Biol.* 1993, 8:20–27.

Burke and Olson "Preparation of clone libraries in yeast artificial–chromosome vectors" in Methods in Enzymology, vol. 194, "Guide to Yeast Genetics and Molecular Biology" eds. C. Guthrie and G. Fink, Academic Press, Inc., Chap. 17, pp. 251–270 (1991).

Capecchi, J.M. et al. "Altering the genome by homologous recombination" *Science,* 1989, 244:1288–1292.

Cregg, J.M. et al. "Recent advances in the expression of foreign genes in *Pichia pastoris*" *Bio/Technology,* 1993, 11:905–910.

Davies et al. "Targeted alterations in yeast artificial chromosomes for interspecies gene transfer" *Nucleic Acids Res.,* 1992, 20(11):2693–2698.

Dickinson et al. "High frequency gene targeting using insertional vectors" *Huamn Molecular Genetics,* 1993, 2(8):1299–1302.

Duff and Lincoln "Insertion of a pathogenic mutation into a yeast artificial chromosome containing the human APP gene and expression in ES cells" *Res. Adv. Alzheimer's Dis. Ref. Disorders,* 1995.

Gilboa, E. et al. "Transfer and expression of cloned genes using retroviral vectors" *Bio Techniques,* 1986, 4(6):504–512.

Hall, C.B. et al. "Immunity to and frequency of reinfection with respiratory syncytial virus" *J. Infec. Dis.,* 1991, 163:693–698.

Huston et al. "Protein engineering of single–chain Fv analogs and fusion proteins" in Methods in Enzymology (JJ Langone, ed: Academic Press, New York, NY), 1991, 203:46–88.

Huxley et al. "The human HPRT gene on a yeast artificial chromosome is functional when transferred to mouse cells by cell fusion" *Genomics,* 1991, 9:742–750.

Jakobovits et al. "Germ–line transmission and expression of a human–derived yeast artificial chromosome" *Nature,* 1993, 362:255–261.

Johnson and Bird "Constructionof single–chain Fvb derivatives of monoclonal antibodies and their production in *Escherichia coli*" in Methods in Enzymology (JJ Langone, ed.: Academic Press, New York, NY), 1991, 203:86–99.

Lamb et al. "Introduction and expression of the 400 kilobase precursor amyloid protein gene in transgenic mice" *Nature Genetics,* 1993, 5:22–29.

Mernaugh and Mernaugh "An overview of phage–displayed recombinant antibodies" in Molecular Methods in Plant Pathology (RP Singh and US Singh, eds.; CRC Press Inc., Boca Raton, FL) 1996 pp. 359–365.

Murry, A. R. and S.F. Dowell "Respiratory syncytial virus: not just for kids" *Hospital Practice,* Jul. 1997, 15:87–104.

Noah, T.L. and S. Becker "Respiratory syncytial virus–induced cytokine production by a human bronchial epithelial cell line" *Am. J. Physiol.,* L472–L478.

Pearson and Choi "Expression of the human b–amyloid precursor protein gene from a yeast artificial chromosome in transgenic mice" *Proc. Natl. Acad. Sci. USA,* 1993, 90:10578–10582.

Persson, C.G. et al. "Epithelium, Microcirculation, and eosinophlis–new aspects of the allergic airway in vivo" *Allergy,* 1997, 52:241–255.

Rothstein "Targeting, disruption, replacement, and allele rescue: integrative DNA transformation in yeast in Methods in Enzymology, Vo. 194, Guide to Yeast GEnetics and Molecular Biology" eds. C. Guthrie and G. Fink, Academic Press, Inc., Chap. 19, pp. 281–301 (1991).

Schedl et al. "A yeast artificial chromosome covering the tyrosinase gene confers copy number–dependent expression in transgenic mice" *Nature,* 1993, 362:258–261.

Stark, J.M. et al. "Respiratory syncytial virus infection enhances neutrophil and eosinophil adhesion to intercellular adhesion molecule–1" *J. Immunol.,* 1996, 156:4774–4782.

Stott, E.J. et al. *J. Virol.,* 1987, 61:3855–3861.

Strauss et al., "Germ line transmission of a yeast artificial chromosome spanning the murine $A_1$ (1) collagen locus" *Science,* 1993, 259:1904–1907.

Subauste, M.C. et al. "Infection of a human respiratory epithelial cell line with rhinovirus. Induction of cytokine release and modulation of susceptibility to infection by cytokine exposure" *J. Clin. Invest.,* 1995, 96:549–557.

Kumasaka et al. *J. Clin. Invest.,* 1996, 97:2362–2369.

Patel, J.A. *Amer. J. Res. Cell Mol. Biol.,* 1995, 13(5):602–609.

\* cited by examiner

INTERRUPTING THE INTERACTION OF INTERCELLULAR ADHESION MOLECULE-1 AND RESPIRATORY SYNCYTIAL VIRUS FOR PREVENTION AND TREATMENT OF INFECTION

CROSS-REFERENCE TO RELATED APPLICATIONS

This application is a continuation of patent application Ser. No. 09/523,054, filed Mar. 10, 2000 now abandoned; which claims the benefit of provisional patent application Ser. No. 60/123,999, filed Mar. 11, 1999; both of which are hereby incorporated by reference in their entirety.

BACKGROUND OF THE INVENTION

1. Field of the Invention

The present invention relates to a method and compound for prevention and/or treatment of respiratory viral infection. More specifically, the present invention relates to blocking Respiratory Syncytial Virus binding to ICAM-1 via agents that interfere with binding or block the expression of ICAM-1.

2. Description of Related Art

Respiratory viruses such as respiratory syncytial virus (RSV), the parainfluenza viruses (PIV), and the influenza viruses cause severe lower respiratory tract diseases in infants and children throughout the world. It is also an important cause of disease in adults and is responsible for a significant amount of excess morbidity and mortality in the elderly. It also can be devastating in immunosuppressed populations (Murray et al., 1997; Pullen et al. 1982; Hall et al. 1984).

Experimental live attenuated vaccines for each of these viruses are being developed for intranasal administration in the first weeks or months of life, but none are currently FDA approved. A variety of RSV, PIV-3, and influenza virus vaccine strains have been developed by classical biological methods, evaluated extensively in preclinical and clinical studies, and shown to be attenuated and genetically stable. However, a major remaining obstacle to successful immunization of infants against respiratory virus associated disease may be the relatively poor immune response of very young infants to primary virus infection. (Crowe J E Jr Vaccine 1998 August–September; 16(14–15):1423–32 Immune responses of infants to infection with respiratory viruses and live attenuated respiratory virus candidate vaccines.)

Moreover, even if one or more vaccines are approved, they may not be suitable for some populations vulnerable to RSV (e.g. very young infants and the immunosuppressed). Ribavirin and immunoglobulin preparations with high titers of RSV-specific neutralizing antibodies are currently approved for use to treat and prevent RSV infection. However, neither of these methods are cost-effective or simple to administer. New agents are needed to reduce the impact of RSV. (Wyde P R Antiviral Res 1998 August; 39(2):63–79 Respiratory syncytial virus (RSV) disease and prospects for its control.

Data obtained from the National Respiratory and Enteric Virus Surveillance System demonstrates the seasonal pattern of RSV infection, with peak rates of 30–40% occurring at the beginning of each year (Murray et al., 1997; Pullen et al. 1982; Hall et al., 1984). RSV infection is commonly associated with interstitial lung diseases, such as bronchiolitis and asthma. It is a major risk factor for a number of other disease conditions, such as immunodeficiency, cardiac arrhythmia, congenital heart disease, and unusual atrial tachycardia (Sly, et al., 1989; Robinson et al. 1997; Armstrong et al. 1993; Fixler, 1996; Lemen, 1995; Persson, 1997; Shelhamer et al. 1995).

Although the severity of the disease decreases with repeated infection, previous RSV infection renders no or limited immunity to subsequent RSV infection (Hal, 1991).

Despite the above serious implications of RSV infection, the progress in the knowledge of the viral genes and gene products (Collins, 1991; Collins et al., 1996; Barik, 1992), an effective vaccine, or treatment against RSV, is yet to be developed.

Additionally, previous attempts to develop a vaccine using formalin inactivated RSV not only failed but exacerbated the disease when subsequent RSV infection occurred (Chanock, et al. 1992; Hall, 1994). An effective vaccine or treatment for RSV would be highly desirable.

Additionally, human nasal, airway, and lung epithelial cells constitute a major target for respiratory infections. Viral infection alters the expression of genes encoding a number of cytokines, chemokines and inflammatory mediators (Sabauste, et al. 1995; Choi, et al. 1992; Becker et al. 1993.

The secretion of cytokines by airway epithelial cells can either initiate local inflammatory responses or amplify an inflammatory event that was previously initiated by activated macrophages, eosinophils, mast cells or lymphocytes (Shelhamer et al., 1995; Holtzman, et al. 1991; Churchill, et al. 1989; Marini, et al. 1992; Churchill, et al. 1992; Kwon, et al. 1994; Sousa, et al. 1994; Cromwell, et al. 1992; Jin, et al. 1997). The epithelial cell-mediated inflammation by involve a number of cytokines and chemokines including IL-1β, IL-6, IL-8, IL-11, IFN-γ, TNF-α, GM-CSF, GRO-α, PLA-2, C3, inducible nitric oxide synthase (iNOS), MCP-1, endothelin-1 (ET-1), mucin, elastase-specific inhibitors, and secretory leukocyte proteinase inhibitor.

The rhinovirus infection of a transformed HBE cell line, BEAS-2B, caused the release of the granulocyte macrophage colony stimulating factor (GM-CSF), IL-6, and IL-8 (Sabauste et al. 1995). The influenza virus infection of primary cultures of human bronchial epithelial (HBE) cells induced the expression of IL-8 (Choi, et al. 1992). Also, in response to RSV infection, nasal epithelial cells and BEAS-2B cells generated IL-8 (Becker et al., 1993; Merolla et al., 1995; Noah, et al., 1993; Garofalo et al. 1996).

It is known that, when infected bronchial epithelial cells secrete several pro-inflammatory cytokines, as set forth above. Some of these cytokines (IL-1β, TNF-2) up-regulate ICAM-1 expression on these cells (Persson et al., 1997; Becker et al., 1993; Noah et al., 1993; Sabauste et al., 1995). ICAM-1, a member of the immunoglobulin gene super family, is a cell surface receptor for the lymphocyte function-associated antigen (LFA-1) adhesion molecule (Makgoba et al., 1998). ICAM-1 mediates the integration of leukocytes into inflammatory sites and facilitates interaction between lymphocytes and target cells. ICAM-1 is also the major cell surface receptor for many of the rhinoviruses (Greve et al., 1989; Staunton et al., 1989; Tomassini et al., 1989).

RSV, though phylogenetically different from rhinovirus, induces a similar profile of cytokines in epithelial cells and also NF-κB, which regulates expression of ICAM-1 that plays a role in neutrophil and eosinophil adhesion to epithelial cells (Arnold et al., 1995; Chini et al., 1998; Stark et al., 1996). Also an elevated expression of ICAM-1 in nasal epithelial cells of asthmatics has been reported (Vignola et al., 1993).

SUMMARY OF THE INVENTION

According to the present invention, there is provided a method of preventing a respiratory infection by administering an effective amount of an agent for regulating ICAM-1 expression. Also provided is a composition for the prevention of respiratory infection including an agent which regulates ICAM expression. method of preventing RSV infection by administering an effective amount of an agent that interferes with the binding of RSV to ICAM-1. A method of preventing RSV infection by administering an effective amount of an agent that down regulates the expression of ICAM-1, thereby decreasing RSV binding to ICAM-1 is also provided. There is provided a method of treating RSV infection by administering an effective amount of an agent for down regulating ICAM-1 expression. A method of blocking RSV-ICAM-1 interaction by administering an effective amount of agents for blocking ICAM sites of binding is provided. Also provided is a compound for blocking RSV-ICAM-1 interaction including an agent for blocking ICAM sites of binding.

DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Generally, the present invention provides a compound and method for protection and prevention against respiratory infection. More specifically, the method provides protection against RSV infection which can be accomplished by administering a pharmaceutically effective amount of an agent.

The agent can be in the form of antibodies to either ICAM-1 or RSV epitopes that interact with the other, antisense oligonucleotides for ICAM-1 or other agents that down regulate ICAM-1 expression, or agents that block RSV interaction with ICAM-1. Specifically, the agent should interfere with the binding of RSV to ICAM-1. By blocking the ICAM sites of binding there is provided protection from RSV infection. Alternatively, the compound of the present invention can be used for the treatment of an RSV infection. In the preferred embodiment, the agent of the present invention blocks the RSV-F binding site on ICAM-1. This has been proven to be the most effective method of prevention and treatment.

The method of the present invention involves administering an effective amount of an agent to a patient sufficient to either prevent the RSV infection or treat the RSV infection. Applicable methods are known to those of skill in the art. Preferably, the agent will be administered to the airway epithelial cells either intranasally or orally. Other methods of administration, as are known to those of skill in the art can be used without departing from the present invention, such as injection or other means of inhalation. Specifically, the present invention provides a method of blocking RSV-ICAM-1 interaction thereby providing protection against the RSV infection by administering an agent with blocking capabilities to a patient in need of such treatment.

Intercellular adhesion molecule-1 (ICAM-1), which is expressed on nasal epithelial cells, is a receptor for rhinovirus and is shown by the inventors to play a role in RSV infection. The role of ICAM-1 in RSV infection was examined using in vitro and in vivo models of RSV infection. Conofocal microscopy indicates that RSV is co-localized with membrane ICAM-1 on cultured, RSV-infected HEp-2 human bronchial epithelial cells.

RSV is also shown by inventors to bind to immobilized ICAM-1. The antibody to RSV-F protein inhibits this binding by 80%, whereas an antibody to RSV-G protein only inhibits by 36%. In a mammalian two-hybrid assay, the RSV-F but not RSV-G gene product interacts with ICAM-1 in transfected NIH3T3 cells. Furthermore, preincubation of HEp-2 cells with a neutralizing monoclonal antibody to CAM-1 inhibits RSV infection of these cells in a dose dependent manner. This antibody also inhibits RSV infection of primary normal human bronchial epithelial cells and transformed epithelial (A549) and macrophage (U937) cell lines. Moreover, mice deficient in ICAM-1 or treated with antibodies and anti-sense oligonucleotides for ICAM-1 are significantly ($p<0.01$) protected against RSV infection. Thus antibodies to RSV, ICAM-1 and ICAM-1 anti-sense oligonucleotides inhibit RSV-ICAM-1 binding and prevents infection.

The compounds of the present invention are administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art. Additionally, when the compound is being administered orally, there must be included a compound for preventing the degradation of the agent.

The agent is administered and dosed in accordance with good medical practice, taking into account the clinical condition of the individual patient, the site and method of administration, scheduling of administration, and other factors known to medical practitioners. The "effective amount" for purposes herein is thus determined by such considerations as are known in the art.

A gene therapy according to the present invention is administered to the airways, e.g. nose, sinus, throat and lung, for example, as nose drops, by nebulization, vaporization or other methods known in the art.

In another embodiment of the present invention, the treatment includes administering to the patient an effective amount of a composition containing a recombinant construct comprising a nucleic acid sequence encoding the agent, the nucleic acid sequence being operatively linked to one or more transcription control sequences. Further, the nucleic acid sequence is expressed at or adjacent to respiratory epithelial cells and the agent results in reduced proliferation of the respiratory infection.

Another embodiment of the present invention relates to a method of protecting a host against respiratory infection by administering to the host an effective amount of a vector containing a construct having a nucleotide sequence encoding the agent with a promoter sequence operatively attached thereto. Further, this construct contains a noninfectious, nonintegrating DNA sequence which controls the expression of the agent. Additionally, administration of the agent is in an amount sufficient to increase levels of the agent in the respiratory tract thus providing a protective response.

The above discussion provides a factual basis for the use of the compound and method for prevention of respiratory viral infection. The methods used with a utility of the present invention can be shown by the following nonlimiting examples and accompanying figures.

EXAMPLES

General Methods:

Gene Therapy:

By gene therapy as used herein refers to the transfer of genetic material (e.g DNA or RNA) of interest into a host with subsequent expression to treat or prevent a disease. The genetic material of interest encodes a product, more specifically it encodes an anti-sense molecule that binds to mucleic acids encoding ICAM-1, thereby preventing its translation. For a review see, in general, the text "Gene Therapy" (Advances in Pharmacology 40, Academic Press, 1997).

According to the method of the present invention, a vehicle/method (transfection, transduction, homologous recombination, etc.) and an expression system as needed and then the modified cells are expanded in culture and returned to the host/patient. These genetically reimplanted cells have been shown to express the transfected genetic material.

In in vivo gene therapy, the genetic material to be transferred is introduced into the cells of the recipient organism in situ, that is within the recipient. These genetically altered cells have been shown to express the transfected genetic material in situ.

The gene expression vehicle is capable of delivery/transfer of heterologous nucleic acid into a host cell. The expression vehicle may include elements to control targeting, expression and transcription of the nucleic acid in a cell selective manner as is known in the art. It should be noted that often the 5'UTR and/or 3'UTR of the gene may be replaced by the 5'UTR and/or 3'UTR of the expression vehicle.

The expression vehicle can include a promotor for controlling transcription of the heterologous material and can be either a constitutive or inducible promotor to allow selective transcription. Enhancers that may be required to obtain necessary transcription levels can optionally be included. Enhancers are generally any non-translated DNA sequence which works contiguously with the coding sequence (in cis) to change the basal transcription level dictated by the promoter. The expression vehicle can also include a selection gene as described herein below.

Vectors can be introduced into cells or tissues by any one of a variety of known methods within the art. Such methods can be found generally described in Sambrook et al., *Molecular Cloning: A Laboratory Manual*, Cold Springs Harbor Laboratory, New York (1989, 1992), in Ausubel et al., *Current Protocols in Molecular Biology*, John Wiley and Sons, Baltimore, Md. (1989), Chang et al., *Somatic Gene Therapy*, CRC Press, Ann Arbor, Mich. (1995), Vega et al., *Gene Targeting*, CRC Press, Ann Arbor, Mich. (1995), *Vectors: A Survey of Molecular Cloning Vectors and Their Uses*, Butterworths, Boston Mass. (1988) and Gilboa et ai (1986) and include, for example, stable or transient transfection, lipofection, electroporation and infection with recombinant viral vectors. In addition, see U.S. Pat. No. 4,866,042 for vectors involving the central nervous system and also U.S. Pat. Nos. 5,464,764 and 5,487,992 for positive-negative selection methods.

Features that limit expression to particular cell types can also be included. Such features include, for example, promoter and regulatory elements that are specific for the desired cell type.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector to be used in the methods of the invention will depend on desired cell type to be targeted and will be known to those skilled in the art.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

The compound of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

The recombinant vector can be administered in several ways. It should be noted that it can be administered as the compound or as pharmaceutically acceptable salt and can be administered alone or as an active ingredient in combination with pharmaceutically acceptable carriers, diluents, adjuvants and vehicles. Local administration can provide a quicker and more effective treatment. Administration can also be performed by, for intranasally orally, subcutaneously or parenterally including intravenous, intraarterial, intramuscular, intraperitoneally, and intranasal administration as well as intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

It is noted that humans are treated generally longer than the mice or other experimental animals exemplified herein which treatment has a length proportional to the length of the disease process and drug effectiveness. The doses may be single doses or multiple doses over a period of several days, but single doses are preferred.

The doses may be single doses or multiple doses over a period of several days. The treatment generally has a length proportional to the length of the disease process and drug effectiveness and the patient species being treated.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

A pharmacological formulation of the compound utilized in the present invention can be administered orally to the patient. Conventional methods such as administering the compounds in tablets, suspensions, solutions, emulsions, capsules, powders, syrups and the like are usable. Known techniques which deliver it orally or intravenously and retain the biological activity are preferred.

In one embodiment, the compound of the present invention can be administered initially by intravenous injection to bring blood levels to a suitable level. The patient's levels are then maintained by an oral dosage form, although other forms of administration, dependent upon the patient's condition and as indicated above, can be used. The quantity to be administered will vary for the patient being treated and will vary from about 100 ng/kg of body weight to 100 mg/kg of body weight per day and preferably will be from 10 mg/kg to 10 mg/kg per day.

Local administration is advantageous because there is no dilution effect and, therefore, a smaller dose is required to achieve expression in a majority of the targeted cells. Additionally, local inoculation can alleviate the targeting requirement required with other forms of administration since a vector can be used that infects all cells in the inoculated area. If expression is desired in only a specific subset of cells within the inoculated area, then promoter and regulatory elements that are specific for the desired subset can be used to accomplish this goal. Such non-targeting vectors can be, for example, viral vectors, viral genome, plasmids, phagemids and the like. Transfection vehicles such as liposomes can also be used to introduce the non-viral vectors described above into recipient cells within the inoculated area. Such transfection vehicles are known by one skilled within the art.

Example 1

Materials and Methods

Cell culture, virus and infection. Bronchial epithelial cells, HEp-2 (ATCC CCL-23), and RSV A2 strain (VR-1302) were obtained from the ATCC, Rockville, Md. HEp-2 cells were grown at 37° C. with 5% $CO_2$ in a minimum essential medium with Hank's salt, supplemented with 5% fetal bovine serum (FBS). HEp-2 cells were infected with RSV at $5 \times 10^5$ pfu/ml and left for absorbtion for 2 h at 37° C. with 5% $CO_2$, after which the virus inoculum was replaced by complete medium. Cells were trypsinized and harvested at various hours post infection. RSV infection was detectable as early as 4 hours post infection by RT-PCR using primers for RSV-N gene (Hegele et al., 1994). Also, the RSV-infected cells could be enumerated by fluorescence microscopy using FITC-conjugated antibodies to RSV.

Confocal microscopy. RSV infected ($5 \times 10^5$ pfu/ml) HEp-2 cells grown on coverslips for 24 hours were fixed in ethanol, blocked for 1 hour with 1% BSA in PBS, pH 7.4 and double stained with goat anti-RSV polyclonal Abs and mouse anti-human [cam-1 MaB (bba4) Each at 4 $\mu$g/ml (R & D Systems, Minneapolis, Minn.) for 1 hour at 37° C. The cells were subsequently incubated for 1 hour with secondary antibodies: rabbit anti-goat IgG-PE conjugate and sheep anti-mouse Igg-FITC conjugate, and were finally mounted in DAPI antifade (Oncor, Gaithersburg, Md.). The cells were scanned using an Oncor digital confocal microscope at 525 nm for FITC, at 580 nm for PE, at 350 nm for DAPI for counter staining of DNA; all three images were merged to confirm the co-localization of ICAM-1 and RSV in the same cell.

Assay for RSV-ICAM-1 Interaction. Soluble CAM-1 protein (R & D Systems, Minneapolis, Minn.) was coated onto high affinity ELISA plates (Costar, Cambridge, Mass.) at 4° C. over night at 100 ng/well in carbonate bicarbonate buffer, pH 9.5. All other incubations were done for 2 hours at 37° C. Wells were blocked in 1% BSA in PBS, pH 7.4 and then incubated with different dilutions of RSV (from $2 \times 10^5$ to $4 \times 19^6$ pfu/ml). For competition, RSV was either preincubated or simultaneously incubated with either anti-RSV-G mAb or anti-RSV-F mAb (20 to 100 $\mu$g/ml). Wells were washed in BSA-Tween-20 (0.1%), pH 7.4 and sequentially incubated with goat anti-RSV polyclonal Ab at 90 $\mu$g/ml (Chemicon, Temecula, Calif.) and anti-goat IgG HEP conjugate (Sigma, St. Louis, Mo.). Wells were washed and developed with the TMB (substrate). Color development was stopped after 30 minutes by addition of 0.2 M sulfuric acid. The optical density was measured at 450 nm.

Flow cytometry. HEp-2 cells were infected with RSV, which had been preincubated with mAb to either F or G, or mouse IgG at 4° C. overnight with gentle shaking. Cells were harvested 24 hours post infection, washed in old PBS, pH 7.4 and incubated with goat anti-RSV polyclonal Ab (Chemicon, Temecula, Calif.) at 1:100 dilution for 1 hour on ice. Cells were then washed with 1 ml of FACS buffer (PBS, pH 7.4: 0.5% FBS; 1 mM EDTA) and incubated with rabbit anti-goat IgG PE conjugate for 1 hour on ice. Cells were again washed in FACS buffer and analyzed for RSV infected cells on a FACScan instrument (Becton Dickinson, Mountain View, Calif.).

Mammalian two-hybrid assay. Full-length cDNAs encoding human [CAM-1, RVS-F and RVS-G were amplified from mRNA of RSV infected HEp-2 cells using gene specific primers, each of which included an appropriate restriction site for subsequent cloning [ICAM-1: Forward-5'CCT GGC GAA TTC CAG ACA TCT GTG TCC CCC TCA (SEQ ID NO: 1), Reverse-5'GTG TGG ATC CAC TGC CAC CAA TAT (SEQ ID NO: 2); F gene: Forward-5'CAA GAA TTC ATG GAG TTG CTA ATC CTC AAA CA (SEQ ID NO: 3), Reverse-5'CTA TGT CGA CTT AGT TAC TAA ATG CAA TAT TAT TTA (SEQ ID NO: 4); and G gene: Forward-5'AAT GAA TTC ATG TCC AAA AAC AAG GAC CAA CGC (SEQ ID NO: 5), Reverse-5'GTT GTC GAC TAA CTA CTG GCG TGG TGT GTT (SEQ ID NO: 6)]. The ICAM-1 cDNA was cloned in-frame with the activation domain (AD) derived from VP16 protein of herpes simplex virus in the vector pVP16 (Clontech, Palo Alto, Calif.). The cDNA encoding F or G protein was amplified, and cloned in frame to the GAL4 DNA-binding domain (DBD) of the pM vector. The orientation and the reading frame of all these fusion constructs were verified to be correct by restriction endonuclease analysis. The pG5CAT vector was used to detect protein-protein interaction by expression of CAT enzyme. CAT activity was assayed using ELISA (Boehringer Mannheim, Indianapolis, Ind.) following the manufacture's protocol. The vectors, pM, pVP16 and pG5CAT, were transfected into NIH 3T3 fibroblast cells to determine the basal level of CAT activity.

ICAM-1 blocking in vitro. HEp-2 cells ($10^5$ cells/ml) were treated with different concentrations (100 to 400 $\mu$g/ml) of anti-ICAM-1 mAb (BBA 4) (R & D Systems, Minneapolis, Minn.) or purified mouse $IgG_1$ antibodies (isotype control) (Sigma, St. Louis, Mo.) for 3 hours at 37° C. and were subsequently infected with RSV at $5 \times 10^5$ n pfu/ml. Cells were harvested 24 hours post-infection.

Reverse transcriptase PCR analysis. The total RNA was isolated from the harvested cells and tissue samples using Trizol (Life Tech., Gaithersburg, Md.). Random printed cDNA was prepared using superscript II RNAse H-reverse transcriptase (Life Tech., Gaithersburg, Md.). The first strand cDNA product (1 $\mu$l) was amplified using Taq polymerase (Life Tech., Gaithersburg, Md.). Forward and reverse primers used are as follows: RSV-N forward: 5'GCG ATG TCT AGG TTA GGA AGA A-3'(SEQ ID NO: 7); reverse: 5'-GCT ATG TCC TTG GGT AGT AAG CCT-3'(SEQ ID NO: 8) (Vignola et al., 1993); ICAM-1 forward: 5'-ATG GCT CCC AGC AGC CCC-3'(SEQ ID NO: 9); reverse: 5'-CAC CTG GCA GCG TAG GGT-3'(SEQ ID NO: 10) and β-actin forward: 5'-CGC GAG AAG ATG ACC CAG-3'(SEQ ID NO: 11); reverse: 5'-ATC ACG ATG CCA GTG GTA C-3'(SEQ ID NO: 12) ALL PCR reactions were denatured at 95° C. for 1', annealed at 56° C. for 1' and extended at 72° C. for 1 minute for 40 cycles. All amplifications were RNA specific, as no bands were seen in the control (no template) PCR samples. The reaction products were separated on 1.5% agarose gels.

Immunofluroscence. RSV infected HEp-2 cells 24 hours post-infection were fixed in chilled acetone for 10 minutes and air-dried. Cells were stained for 30 minutes at 37° C. with FITC-labeled anti-RSV mAbs (Chemicon, Temecula, Calif.) in a humid chamber. The unbound antibodies were removed by washing three times in PBS-Tween-20 (0.2%) buffer, pH 7.4. The slides were air dried again and mounted on Fluromount G (Fisher, Pittsburgh, Pa.) and observed under fluorescent microscope. RSV positive cells (green fluorescence) were counted randomly from 15 different spots and from two different slides for the same treatment group and the percent of infected cells were plotted against the concentration of ICAM-1 mAb.

Animals and Virus Infection. All animal experiments were performed in accordance with protocols approved by the University of South Florida and James A. Haley Veteran's Hospital Animal Care Committee. Mice were obtained from Jackson Laboratory (Bar Harbor, Me.) and maintained in pathogen free condition. Mice were infected with 50 $\mu$l RSV suspension ($5 \times 10^5$ pfu/ml) under light anesthesia of Nembutal (Abbot Laboratories, North Chicago, Ill.) by intranasal administration. The pattern of RSV induced lung infection in mice was similar to the published reports (Anderson et al., 1990; Oppenshaw et al., 1995; Hsu et al., 1998).

ICAM-1 blocking in vivo. Mice were first intra-tracheally administered with the mixture of ICAM-1 pholphothioate ant-sense ODNs (300 $\mu$g/mouse) complexed with the cationic lipid, lipofectamine (2.5 $\mu$g ODN/$\mu$g lipofectamine), and goat anti-mouse ICAM-1 mAb (40 $\mu$g mouse). After 2 hours the same mice were inoculated intranasally with goat anti-mouse ICAM-1 mAb (50 $\mu$g mouse) and infected with RSV 2 hours post-treatment. Mice were sacrificed two days post-infection and lungs were collected to examine RSV replication in lung cells by RT-PCR.

Histopathology. Viral infection, immunohistopathology and scoring inflammatory lesions were performed as described (Tayler et al., 1984; Graham et al., 1988) with modifications. Mice were sacrificed on the fourth day post infection (pi) by overdose (0.6 g/kg) of pentobarbital. Lungs were inflated via trachea, fixed in Zamboni's PAF fixative at 4° C. for 24 hours and subsequently transferred to 80% ethanol followed by paraffin embedding. The sections were stained with hematoxylin and eosin (HE). The slides were coded and scored in blind fashion twice each by three different individuals. The severity of lung pathology was scored on a scale of 0–3 indicating the degree of inflammation. The entire lung section was reviewed and pathological changes were evaluated for epithelial damage, peribronchovascular cell infiltrate and interstitial-alveolar cell infiltrate from both the ICAM-1$^{+/+}$ and ICAN-1$^{-/-}$ mice. Epithelial damage was scored as: 0=no damage, 1=increased cytoplasm of epithelial cells without desquamation, 2=epithelial desquamation without bronchial exudate composed of inflammatory cells, 3=bronchial exudate composed with desquamated epithelial cells and inflammatory cells. Peribronchovascular cell infiltrate was scored as: 0=no infiltrate, 1=infiltrate up to four cells, 2=infiltrate five to ten cells, 3=infiltrate more than ten cells. Interstitial-alveolar cell infiltrate was scored as: 0=no infiltrate, 1=mild, generalized increase in cell mass of the alveolar septa without thickening of the septa or significant airspace consolidation, 2=dense septal infiltrate with thickening of septa, 3=significant alveolar consolidation in addition to interstitial inflammation. Pathological scores were expressed as mean±standard error of mean (SEM). Intraobserver variation was <5%.

Statistical analysis. The difference between the treated and control cells was analyzed by Student's t test. The percent infection between groups of mice was compared with chi-square test.

Pathological scores were expressed as mean±standard error of mean (SEM) and statistical comparisons between two groups were made with Mann-Whittney Test. Differences between groups were considered significant as ρ values less than 0.05. All analyses were performed on a Macintosh Computer (Apple Computer Inc., Cupertino, Calif.) with Startview II software (Abacus Concepts, Berkely, Calif.).

Results and Discussion

Figure 1:
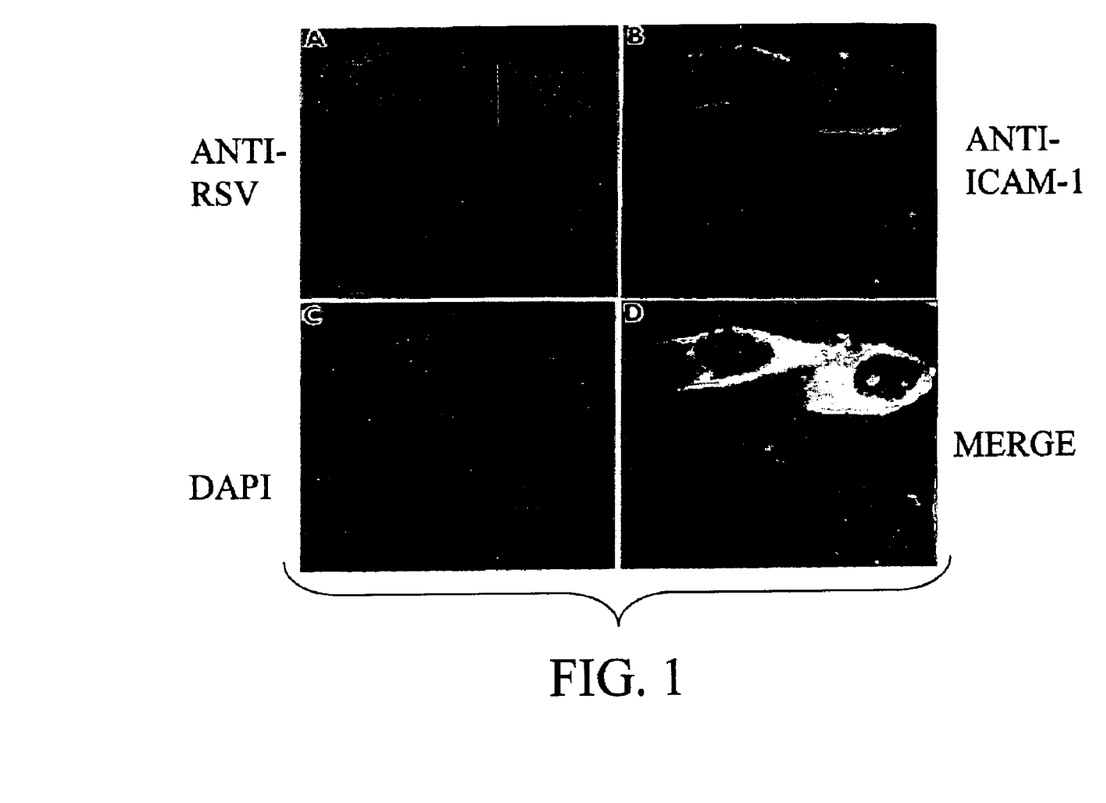
FIG. 1 is a photograph showing the topography of ICAM-1 expression in RSV infected HEp2 cells by confocal microscopy.

Surface ICAM-1 expression on HEp-2 cells infected with RSV was assayed following RSV infection by flow cytometry. The uninfected HEp-2 cells showed constitutive expression (3.6%) of ICAM-1. Surface ICAM-1 expression increased by four and eight fold, respectively, 24 hours and 48 hours post RSV infection. RSV antigen expression was detected both on the plasma membrane and in the cytoplasm as determined by confocal microscopy, whereas ICAM-1 expression was localized mostly to the plasma membrane (FIG. 1). The co-localization of RSV And ICAM-1 ON HEp-2 cell surfaces (FIG. 1D) suggested that RSV directly binds to ICAM-1 on epithelial cells.

More specifically, FIG. 1 shows the topography of ICAM-1 expression in RSV-infected HEp-2 cells by confocal microscopy as described (Fixler, 1996). FIG. 1A shows that RSV was distributed on the cell surface and in the cell cytoplasm (red), FIG. 1B shows that ICAM-1 was localized mostly on the cell surface by FITC staining (green), and FIG. 1C shows that the nuclei were visualized by staining with DAPI (blue). FIG. 1D shows that superimposition of all the three images indicated the co-localization of RSV and ICAM-1 on the plasma membrane of RSV infected cells.

Figure 2A:
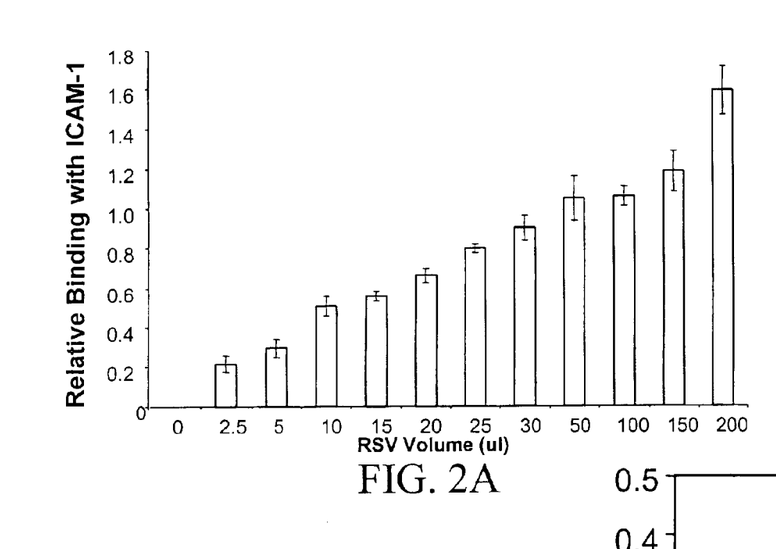
FIGS. 2A–B are graphs showing the interaction of ICAM-1 with RSV; (A) shows RSV bound to and immobilized ICAM-1 in a dose dependent manner; (B) shows the inhibition of RSV binding to ICAM which is examined by pre-incubation of RSV with mAbs.
Figure 2B:
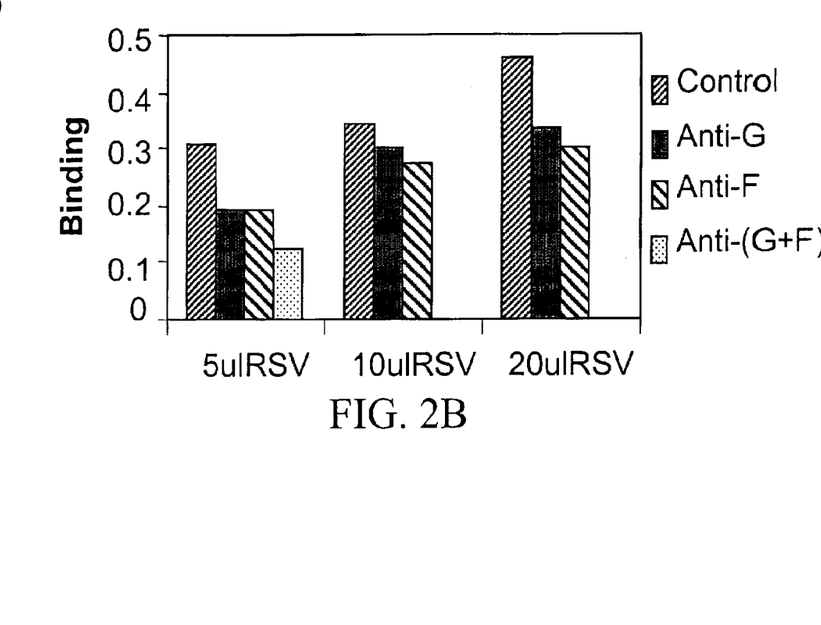

The direct binding of RSV to ICAM-1 was examined by ELISA. RSV bound to immobilized ICAM-1 in a dose-dependent manner (FIG. 2A). The lack of ICAM-1 binding to conditioned medium in absence of RSV (control) indicated that the binding between ICAM-1 and RSV in specific (FIG. 2A). *Pneumoviruses* encode two major surface glycoproteins, the G protein that presumably attaches to the cell surface receptor (Levine et al., 1987) and the F protein that mediates fusion of viral envelope to cell membrane (Hall et al., 1991). Antibodies to either G or F protein neutralize virus infectivity and seem to play a major role in protective immunity against RSV both in human and mice (Olmsted et al., 1986; Stott et al., 1987). To determine which of these RSV proteins interacts with ICAM-1, the RSV suspension was incubated with mAb to either F or G and the degree of inhibition of RSV binding to ICAM-1 was assayed. Incubation with mAb to either F or G decreased the RSV-ICAM-1 binding by 80% and 36%, respectively (FIG. 2B). These results show that RSV can bind to ICAM-1 in the absence of other cellular factors and that the RSV binds to ICAM-1 primarily via its F protein.

The role of F vis-à-vis G protein on the binding of RSV to ICAM-1 on HEp-2 cells was investigated. RSV was incubated with mAb to F or G protein or mouse IgG$_1$ (control) and then used to infect HEp-2 cells and the percent of infected cells estimated by flow cytometry. Compared to control Abs, the mAb to F significantly inhibited (73.8%) the RSV infection of HEp-2 cells G protein, whereas the mAb to G did not. Furthermore, direct interaction of F or G protein with ICAM-1 protein was assayed by estimating chloramphenicol acetyl transferase (CAT) expression in a mammalian two-hybrid system. The transfection of NIH3T3 fibroblast cells with cDNA constructs expressing G, wherein ICAM-1 and CAT (pG5CAT) resulted in CAT activity similar to the basal level. In contrast, co-transfection of these cells with cDNA constructs expressing F, wherein ICAM-1 and CAT vectors resulted in a two-fold increase compared to is basal CAT activity showing that interaction of RSV with ICAM-1 is mediated by F protein. Together, these results show that F protein binds to ICAM-1. The finding that the F and not G protein binds to ICAM-1 is consistent with the result noted and with other reports that antibodies to F protein have greater neutralizing ability than antibodies to G protein (Graham et al., 1988; Levine et al., 1987; Hall et al., 1991; Olmsted et ai., 1986; Stott et al., 1987).

Figure 3A:
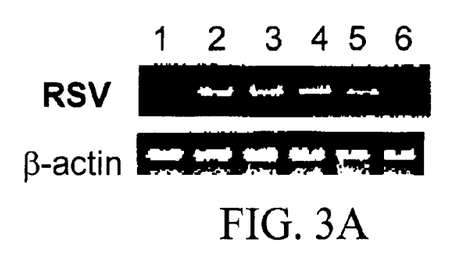
FIGS. 3A–C are photographs showing the anti-ICAM-1 mAb treatment and how it inhibits RSV infection in airway epithelial cells.

To explore the possibility that blocking of ICAM-1 would inhibit the initiation of RSV infection. HEp-2 cells were infected with RSV after having been incubated with various concentrations of a mAb to human ICAM-1. Since RSV infection begins when live RSV replicates in the host cell; the intracellular viral replication was determined 24 hours post infection using RT-PCR analysis for the expression of mRNA of the RSV nucleocapsid (N) gene. Preincubation of HEp-2 cells with anti-ICAM-1 inhibited amplifiable mRNA levels in a dose-dependent manner, with the greatest inhibition (70% compared to control) observed using a concentration of 400 μg of anti-ICAM-1 mAb/ml medium (FIG. 3A). The reduction in virus replication was correlated with the RSV titers in the supernatant as determined by ELISA.

Figure 3B:
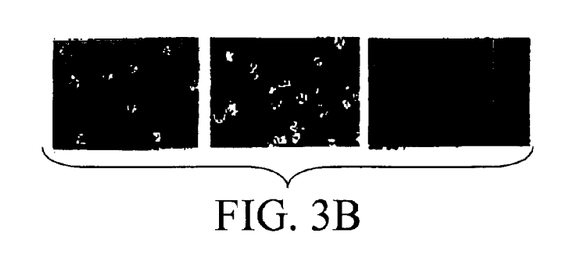

Inhibition of RSV infection was also determined by immunofluorescence by scoring the RSV-infected cells stained with FITC-labeled mAb to RSV. Cells were counted randomly from fifteen different spots from two different slides of each group and the percentage of infected cells plotted against the concentration of anti-ICAM-1 mAb (FIG. 3B). A dose-dependent reduction in the number of infected cells occurred with increasing concentrations of anti- ICAM-1 mAb and the greatest inhibition of infection (96%) was observed at 400 μg/ml of ant-ICAM-1 mAb. In contrast, pre-incubation with the same concentration of isotype matched control antibodies showed no significant reduction in RSV replication. Two other cell lines, A549 (ATCC) and NHBE (Clonetics, San Diego, Calif.), were examined for inhibition of RSV infection by anti-ICAM-1 mAb, to exclude the inhibition an HEp-2 cell specific phenomenon NHBE is a normal human primary cell line derived from bronchial explants, whereas A549 is a transformed lung type II alveolar epithelial cell line. NHBE and A549 exhibited significant reductions (54% and 67%, respectively) in RSV is infection when they were preincubated with 400 μg of anti-ICAM-1 mAb/ml (FIG. 3B). These two cell lines differed from HEp-2 cells in the magnitude of RSV infection and inhibition of RSV infection. HEp-2 cells showed the greatest infection and inhibition of infection among the cell lines examined. The fact that preincubation of epithelial cells with anti-ICAM-1 mAb significantly inhibited both RSV replication and RSV infection indicates that ICAM-1 may be the principal molecule required for the initiation of RSV infection in these cells.

Figure 3C:
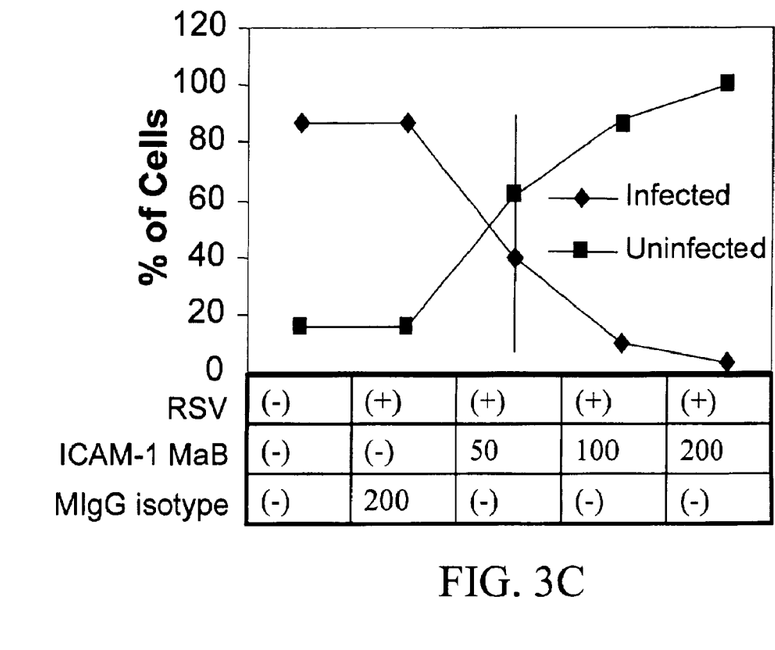

More specifically, FIG. 3 shows anti-ICAM-1 mAb treatment inhibits RSV infection in airway epithelial cells. In FIG. 3(A), preincubation of HEp-2 cells with anti-ICAM-1 mAb inhibited the expression of the RSV N gene. HEp-2 cells were treated either with anti-ICAM-1 mAb 100 μg/ml (lane 4), 200 μg/ml (lane 5) or 400 μg/ml (lane 6), or mouse IgG$_1$ antibody (control) 400 μg/ml (lane 3), and subsequently infected with RSV (lanes 2–6 (Staunton et al., 1989). Total RNA was subjected to RT-PCR analysis using primers for the RSV N gene and β-actin (as internal control). RT-PCR products were quantified by densitometry, and the band intensity relative to β-actin was plotted (lower panel). In FIG. 3(B), anti-ICAM-1 mAb treatment inhibited RSV infection of epithelial cells. The percent of RSV infected HEp-2, NHBE and A549 cells after pre-incubation with anti-ICAM-1 mAb or an isotype control Ab was estimated as described (Tomassini et al., 1989). Each value represents mean±SEM. The experiment was repeated for each cell line with similar results. A representative experiment for each of the cell lines is shown. FIG. 3C shows inhibition of mRNA expression for RANTES and ET-1 by pretreatment of HEp-2 cells with anti-ICAM-1 mAb prior to infection. Total RNA was subjected to RT-PCR analysis using primers for RANTES, ET-1 and β-actin for each treatment (lanes 1–6 as described in A) was plotted.

Figure 4A:
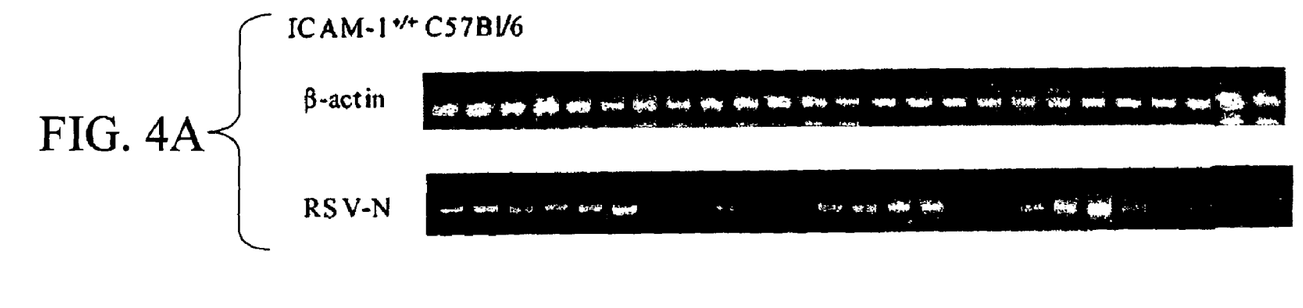
FIGS. 4A–B show the role of ICAM-1 in a murine model of RSV infection; the C57B1/6 wildtype and ICAM-1 KO mice were inoculated i.n. with RSV then after 4 days the mice were sacrificed and the lungs were taken out; RT-PCR was done to check the replication of RSV in the lung tissue of ICAM-1 KO and the wild type mice using the method set forth in the present invention.

To examine the in vivo role of ICAM-1 in the initiation of RSV infection, a murine model of RSV infection was adapted using C57B1/6 and BALB/c mice. Intranasal administration of RSV to C57BL6 and BALB/c mice induced lung infection, which peaked between day three and seven post infection. RSV replication was detectable in lung cells two to four days post infection, utilizing Rt-PCR, as described for HEp-2 cells. ICAM-1 deficient (ICAM-1$^{-1-}$) mice were is used to evaluate the role of ICAM-1 in the initiation of RSV infection (Sligh et al., 1993). The RT-PCR analysis of RSV N gene mRNA demonstrated that in contrast to 52% (13/25) of C57BL6-ICAM-1$^{-/-}$, 88% (22/25) of the wild type (ICAM-1$^{+/+}$)mice permitted RSV replication in their lung tissue (FIG. 4A). These results indicate a significant role of ICAM-1 in the initiation of RSV infection.

Figure 4B:
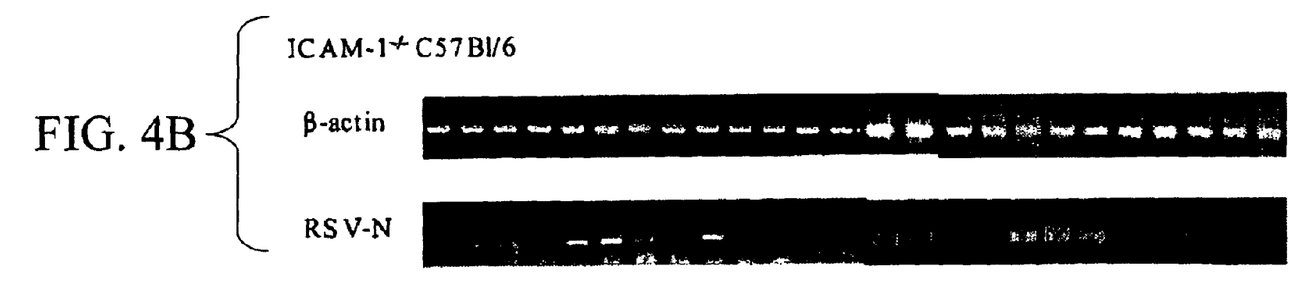

ICAM-1 antibodies and anti-sense oligodeoxynucleotides (ODNs) were previously found to protect mice from septic shock by decreasing pulmonary inflammation (Kumasaka et al., 1996) and the magnitude of protection ranged from 58 to 75% of control. However, the role of anti-ICAM-1 mAbs and ODNs against the initiation of RSV infection has not been previously examined. To confirm the in vivo role of ICAM-1 in RSV infection, BALB/c mice were intratracheally administered a combination of anti-ICAM-1 mAb and ICAM-1 anti-sense ODNs and subsequently infected with RSV. The RSV infection was monitored by RT-PCR of RSV-N gene mRNA from lung homogenate. The results demonstrate that pretreatment of BALB/c mice with a combination of ICAM-1 anti-sense ODNs and anti-ICAM-1 mAb decreased RSV N mRNA expression by 84% anti-ICAM-1 mAb decreased RSV N mRNA expression by 84% in RSV infected mice (FIG. 4B). These results confirm that the presence of ICAM-1 enhances the successful initiation of RSV infection in vivo.

More specifically, FIG. 4 shows the analysis of RSV infection in mice. FIG. 4(A) shows the RT-PCR analysis of the lung mRNA of RSV infected ICAM-1$^{+/+}$ and ICAM-1$^{-/-}$ C57BL6 mice (n=25 each) using RSV-N gene specific primers. FIG. 4(B) shows the RT-PCR analysis of RSV infection in the lung RNA of BALB/c mice pre-treated with ICAM-1 anti-sense ODNs and anti-ICAM-1 mAb (lanes 1–4, PBS treated; and lanes 5–8, treated with mAb and ODNs) and subsequently infected with RSV (Oppenshaw 1995). Lung tissues were examined for replication by RT-PCR for RSV-N and β-actin (upper panel). RT-PCR products were quantified by densitometry, and the band intensity relative to β-actin for each mouse was plotted (Lower panel). FIG. 4(C) shows RSV-induced lung pathology was evaluated for epithelial cell damage, interstitial-alveolar and peribronchovascular infiltrations (Vignola et al., 1993). The bars represent mean±SEM; the asterics indicate the level significance at p<0.05; open circles, sham-infected ICAM-1$^{+/+}$; closed circles, sham-infected ICAM-1$^{-/-}$; open triangles, RSV-infected ICAM-1$^{+/+}$; closed triangles, RSV-infected ICAM-1.

Histopathology of the lung sections of the ICAM-1$^{-/-}$ and ICAM-1$^{+/+}$ mice [for each infected (n=13) and sham infected (n=8)] were analyzed to determine the pattern of inflammation induced by RSV. Pathological changes were determined by scoring for epithelial damage, interstitial-alveolar infiltrate and peribronchovascular infiltrates (FIG. 4C). RSV infected ICAM-1$^{-/-}$ mice exhibited significantly less (p<0.05) epithelial damage and interstitial-alveolar cellular infiltration compared to the ICAM-1$^{+/+}$ mice. No significant difference was seen in peri-bronchovascular infiltration between ICAM-1$^{-/-}$ and ICAM-1$^{+/+}$ mice. These results show that ICAM-1 deficiency provides a significant but only partial protection against inflammation due to RSV infection, similar to attenuated responses reported for neutrophil emigration in chemical peritonitis, in ischemic injury and septic shock in ICAM-1$^{-/-}$ mice (Sligh et al. 1993; Kelly et al., 1996; Xu et al., 1994). The protection in all of these disease models is believed to be primarily due to the role of ICAM-1 in mediating infiltration of inflammatory cells into the lung.

A significant finding from these studies is that ICAM-1 plays a pivotal role in the initial steps of RSV infection. RSV binds to ICAM-1 on the cell surface via its F protein. Blocking ICAM-1 with a neutralizing anti-ICAM-1 mAb or RSV with a mAb to F protein significantly inhibits RSV infection both in in vitro and in vivo models. Although these studies were confined to the RSV strain A$_2$, RSV are considered serologically monotypic, i.e., antiserum to A$_2$ neutralizes heterologous strains in in vitro assays and in experimental animals (Graham et al., 1988; Levine et al., 1987; Hall et al., 1991). The inventor's demonstration that a combination of anti-ICAM-1 mAb and ICAM-1 antisense ODNs prevented RSV infection of the lung cells in mice suggests that ICAM-1 mediation of RSV infection is not an epithelial cell specific phenomenon. Preincubation of a human macrophage cell line, U937, also inhibited RSV infection of these cells. Since RSV F-ICAM-1 binding is pivotal to RSV entry into the host cells, RSV can be neutralized using a soluble ICAM-1 may be potentially useful.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the described invention, the invention may be practiced otherwise than as specifically described.

REFERENCES

Burke and Olson, "Preparation of Clone Libraries in Yeast Artificial-Chromosome Vectors" in *Methods in Enzymology*, Vol. 194, "Guide to Yeast Genetics and Molecular Biology", eds. C. Guthrie and G. Fink, Academic Press, Inc., Chap. 17, pp. 251–270 (1991).

Capecchi, "Altering the genome by homologous recombination" *Science* 244:1288–1292 (1989).

Davies et al., "Targeted alterations in yeast artificial chromosomes for interspecies gene transfer", *Nucleic Acids Research*, Vol. 20, No. 11, pp. 2693–2698 (1992).

Dickinson et al., "High frequency gene targeting using insertional vectors", *Human Molecular Genetics*, Vol. 2, No. 8, pp. 1299–1302 (1993).

Duff and Lincoln, "Insertion of a pathogenic mutation into a yeast artificial chromosome containing the human APP gene and expression in ES cells", *Research Advances in Alzheimer's Disease and Related Disorders,* 1995.

Huxley et al., "The human HPRT gene on a yeast artificial chromosome is functional when transferred to mouse cells by cell fusion", *Genomics*, 9:742–750 (1991).

Jakobovits et al., "Germ-line transmission and expression of a human-derived yeast artificial chromosome", *Nature*, Vol. 362, pp. 255–261 (1993).

Lamb et al., "Introduction and expression of the 400 kilobase precursor amyloid protein gene in transgenic mice", *Nature Genetics*, Vol. 5, pp. 22–29 (1993).

Pearson and Choi, Expression of the human b-amyloid precursor protein gene from a yeast artificial chromosome in transgenic mice. Proc. Natl. Acad. Sci. USA, 1993. 90:10578–82.

Rothstein, "Targeting, disruption, replacement, and allele rescue: integrative DNA transformation in yeast" in *Methods in Enzymology*, Vol. 194, "Guide to Yeast Genetics and Molecular Biology", eds. C. Guthrie and G. Fink, Academic Press, Inc., Chap. 19, pp. 281–301 (1991).

Schedi et al., "A yeast artificial chromosome covering the tyrosinase gene confers copy number-dependent expression in transgenic mice", *Nature*, Vol. 362, pp. 258–261 (1993).

Strauss et al., "Germ line transmission of a yeast artificial chromosome spanning the murine $a_1$ (I) collagen locus", *Science*, Vol. 259, pp. 1904–1907 (1993).

Gilboa, E, Eglitis, M A, Kantoff, P W, Anderson, W F: Transfer and expression of cloned genes using retroviral vectors. BioTechniques 4(6):504–512, 1986.

Cregg J M, Vedvick T S, Raschke W C: Recent Advances in the Expression of Foreign Genes in *Pichia pastoris*, Bio/Technology 11:905–910, 1993.

Culver, 1998. Site-Directed recombination for repair of mutations in the human ADA gene. (Abstract) Antisense DNA & RNA based therapeutics, February, 1998, Coronado, Calif.

Huston et al, 1991 "Protein engineering of single-chain Fv analogs and fusion proteins" in Methods in Enzymology (J J Langone, ed.; Academic Press, New York, N.Y.) 203:46–88.

Johnson and Bird, 1991 "Construction of single-chain Fvb derivatives of monoclonal antibodies and their production in *Escherichia coli* in Methods in Enzymology (J J Langone, ed.; Academic Press, New York, N.Y.) 203:88–99.

Mernaugh and Mernaugh, 1995 "An overview of phage-displayed recombinant antibodies" in Molecular Methods In Plant Pathology (R P Singh and U S Singh, eds.; CRC Press Inc., Boca Raton, Fla.) pp. 359–365.

Collins, P. L. 1991. The molecular biology of human respiratory syncytial virus (RSV) of the genus Pneumovirus. In *The Paramyxoviruses*. D. W. Kingsbury, Editor, Plenum, N.Y., 1991.103–162.

Murray, A. R., and S. F. Dowell. 1997. Respiratory syncytial virus: not just for kids. *Hospital Practice*, July 15:87–104.

Center for Disease Control and Prevention: Respiratory syncytial virus activity: United States. 1996–1997 season, *MMW* 45:1053, 1996.

Sly, P. D., and M. E. Hibbrt. 1989. Childhood asthma following hospitalization with acute viral bronchiolitis in infancy. *Pediatr. Pulmonol.* 7:153–158.

Jeng, M. J., and R. J. Lemen 1997. Respiratory syncytial virus and bronchiolitis. *Am. Fam. Physician.* 55: 1139–1146.

Armstrong, D. S., and S. Menahem. 1993. Cardiac arrythmias as manifestation of acquired heart disease in association with pediatric respiratory syncytial virus infection. *J. Ped. Child Health* 29:309–311.

Fixler, D. E. 1996. Respiratory syncytial virus infection in children with congenital heart disease. *Ped. Cardiol.* 17:163–168.

Persson, C. G., J. S. Erjefalt, M. Anderson, I. Erjefalt, L. Greiff, M. Korsgren, M. Linden, F. Sundler, and C. Svensson. 1997. Epithelium, microcirculation, and eosinophils-new aspects of the allergic airway in vivo. *Allergy* 52:241–255.

Becker, S., H. S. Koren, and D. C. Henke. 1993. Interleukin-8 expression in normal nasal epithelium and it modulation by infection with respiratory syncytial virus and cytokines tumor necrosis factor, interleukin-1 and interleukin-6. *Am. J. Respir. Cell Mol. Biol.* 8:20–27.

Noah, T. L., and S. Becker. 1993. Respiratory syncytial virus-induced cytokine production by a human bronchial epithelial cell line. *Am. J. Physiol.* L472–L478.

Sabauste, M. C., D. B. Jacoby, S. M. Richards, and D. Proud. 1995. Infection of a human respiratory epithelial cell line with rhinovirus. Induction of cytokine release and modulation of susceptibility to infection by cytokine exposure. *J. Clin. Invest* 96:549–557.

Makgoba, M. W., M. E. Sanders, G. E. Ginther Luce, E. A. Gugel, M. L. Dustin, T. A. Springer, and S. Shaw. 1998. Functional evidence that intercellular adhesion molecule-1 (ICAM-1) is a ligand for LFA-1 dependent adhesion in T cell-mediated cytotoxicity. *Eur. J. Immunol.* 18:637–640.

Greve, J. M., G. Davis, A. M. Meyer, C. P. Forte, S. C. Yost, C. W. Marlor, M. E. Kamarck, and A. McClelland. 1989. The major human rhinovirus receptor is ICAM-1. *Cell* 56:839–847.

Staunton, D. E., J. Merluzzi, R. Rothlein, R. Barton, S. D. Marlin, and T. A. Springer. 1989. A cell adhesion molecule, ICAM-1, is the major surface receptor for rhinoviruses. *Cell* 56:849–853.

Tomassini, J. E., D. Graham, C. M. Dewitt, D. W. Lineberger, J. A. Rodkey, and R. J. Colonno. 1989. CDNA cloning reveals that the major group rhinovirus receptor on HeLa cells in intercellular adhesion molecule 1. *Proc. Natl. Acad. Sci. USA.* 86:4907–4911.

Chini, B. A., M. A. Fiedler, L. Milligan, T. Hopkins, and J. M. Stark. 1998. Essential roles of NF-kappa B and c/EBP in the regulation of intercellular adhesion molecule-1 after respiratory syncytial virus infection of human respiratory epithelial cell cultures. *J. Virol.* 72:1623–1626.

Stark, J. M., V. Godding, J. B. Sedgwick, and W. W. Busse. 1996. Respiratory syncytial virus infection enhances neutrophil and eosinophil adhesion to intercellular adhesion molecule-1. *J. Immunol.* 156:4774–4782.

Arnold, R., H. Werchau, and W. Konig. 1995. Expression of adhesion molecules (ICAM-1, LFA-3) on human epithelial cells (A549) after respiratory syncytial virus infection. *Int Arch. Allergy Immunol.* 107:392–393.

Vignola, A. M., A. M. Campbell, P. Chanez, J. Bousquet, P. Paul-Lacoste, F. B. Michael, P. Godard. 1993. HLA-DR and ICAM-1 expression on bronchial epithelial cells in asthma and chronic bronchitis. *Am. Rev. Respir. Dis.* 148:689–94.

Hegele, R. G., S. Hayashi, A. M. Bramley, and J. C. Hogg. 1994. Persistence of respiratory syncytial virus genome and protein after acute bronchiolitis in guinea pigs. Chest 105: 1848–1854.

Anderson J. J., J. Nordan, D. Saunders, G. L. Toms, and R. Scott. 1990. Analysis of the local and systemic immune responses induced in BALB/c mice by experimental respiratory syncytial virus infection. *J. Gen. Virol.* 71, 1561–1570.

Oppenshaw, P. J. M. 1995. Immunity and immunopathology to respiratory syncytial virus: the mouse model. *Am. J. Res. Crit. Care Med.* 152, S59–62.

Hsu, S. C., D. Chargelegue, and M. W. Steward. 1998. Reduction of respiratory syncytial virus titer in the lungs of mice after intranasal immunization with a chimeric peptide consisting of a single CTL epitope linked to a fusion peptide. *Virology.* 240, 376–381.

Tayler, G., E. J. Scott, M. Hugh, and A. P. Collins. 1984. Respiratory syncytial virus infection in mice. *Infection and Immunity* 43:649–655.

Graham, B. S., M. D. Perkins, P. F. Wright, and D. T. Karzon. 1988. Primary respiratory syncytial virus infection in mice. J. Med. Virol. 26:153–162.

Levine, S., R. Klaiber-Franco, and P. R. Paradiso. 1987. Demonstration that glycoprotein G is the attachment protein of respiratory syncytial virus. *J. Gen. Virol.* 68:2521–2524.

Hall, C. B., E. E. Walsh, C. E. Long, and K. C. Schnabel. 1991. Immunity to and frequency of reinfection with respiratory syncytial virus. *J. Infec. Dis.* 163:693–698.

Olmsted, R. A, R. M. Chanock, and P. L. Collins. 1986. Expression of the F glycoprotein of respiratory syncytial virus by a recombinant vaccinia virus: comparison of the individual contributions of the F and G glycoproteins to host immunity. *Proc. Natl. Acad. Sci. USA* 83:7462–7466.

Stott, E. J., G. Taylor, L. A. Ball, K. Anderson, K. K. Young, A. M. King, and G. W. Wertz. 1987. Immune and histopathological responses in animals vaccinated with recombinant vaccinia viruses that express individual genes of human respiratory syncytial virus. *J. Virol.* 61:3855–3861.

Li, X., S. Sambhara, C. X. Li, M. Ewasyshyn, M. Parrington, J. Caterini, O. James, G. Gates, R. P. Du, and M. Klein. 1998. *J. Exp. Med.* 188:681–688.

Becker, S. W. Reed, F. W. Henderson, and T. L. Noah. 1997. RSV infection of human airway epithelial cells causes production of the beta-chemokine RANTES. *Am. J. Physiol.* 272 (Lung Cell. Mol. Physiol. 16): L512–L520.

Saito, T., R. W. Deskin, A. Casola, H. Haeberle, B. Olszewska, P. B. Ernst, R. Alam, P. L. Ogra. and R. Garofalo. 1997. Respiratory syncytial virus induces selective production of the chemokine RANTES by upper airway epithelial cells. *J. Infect. Dis.* 175:497–504.

Behera, A. K., M. Kumar, H. Matsuse, R. F. Lockey, and S. S. Mohapatra. 1998. Respiratory syncytial virus induces the expression of 5-lipoxygenase and endothelin-1 in bronchial epithelial cells. *Biochem. Biophys. Res. Commun.* In pres.

Sligh, J. E., C. M. Ballantyne, and S. S. Rich, H. K. Hawkins, C. W. Smith, A. Bradley, and A. L. Beaudet. 1993. Inflammatory and immune responses are impaired in mice deficient in intercellular adhesion molecule-1. *Proc. Natl. Acad. Sci. USA.* 90:8529–8533.

Kelly, K. J., W. W. Williams Jr., R. B. Colvin, S. M. Meehan, T. A. Springer, J. C. Gutierrez-Ramos, and J. V. Bohventre. 1996. Intercellular adhesion molecule-1 deficient mice are protected against ischemic renal injury. *J. Clin. Invest.* 97:1056–1063.

Xu, H., J. A. Gonzalo, Y. St. Pierre, I. R. Williams, T. S. Kupper, R. S. Cotran, T. A. Springer, and J. C. Gutierrez-Ramos. 1994. Leukocytosis and resistance to septic shock in intercellular adhesion molecule-1 deficient mice. *J. Exp. Med.* 180:95–109.

Kumasaka, T., W. M. Quinlan, N. A. Doyle, T. P. Condon, J. Sligh, F. Takei, A. L. Beaudet, C. F. Bennett, and C. M. Doerschuk. 1996. Role of the intercellular adhesion molecule-1 (ICAM-1) in endotoxin-induced pneumonia evaluated using ICAM-1 antisense oligonucleotides, anti-ICAM-1 monoclonal antibodies, and ICAM-1 mutant mice. *J. Clin. Invest.* 97:2362–2369.

Almenar-queralt, A., A. Duperray, L. A. Miles, J. Felez, and D. C. Altieri. 1995. Apical topography and modulation of ICAM-1 expression on activated endothelium. *Am. J. Pathol.* 147:1278–1288.

Staunton, D. E., A. Gaur, P. Y. Chan, and T. A. Springer. 1992. Internalization of a major group human rhinovirus does not require cytoplasmic or transmembrane domains of ICAM-1. *J. Immunol.* 148:3271–3274.

Huguenel, E. D., O. Cohn, D. P. Dockum, J. M. Greve, M. A. Fournel, L. Hammond, R. Irwin, J. Mahoney, A. McClelland, E. Muchmore, A. C. Ohlin, and P. Scuderi. 1997. Prevention of rhinovirus infection in chimpanzees by soluble intercellular molecule-1. *Am. J. Respir. Crit. Care Med.* 155:1206–1210.

Bella, J., P. R. Kolatkar, C. W. Marlor, J. M. Greve, and M. G. Rossmann. 1998. The structure of the two amino-terminal domains of human ICAM-1 suggests how it functions as a rhinovirus receptor and as an LFA-1 integrin ligand. *Proc. Natl. Acad. Sci. USA* 95:4140–4145.

Casanovas, J. M., T. Stehle, J. Liu, J. Wang, and TA. Springer. 1998. A dimeric crystals structure for the N-terminal two domains of intercellular adhesion molecule-1 *Proc. Natl. Acad. Sci. USA* 95:4134–4139.

What is claimed is:

1. A composition for the reduction of respiratory infection comprising an antisense oligonucleotide for human ICAM-1, wherein said composition is an inhalant.

2. A method of preventing RSV infection by administering an effective amount of the composition of claim 1 to a patient, wherein the antisense oligonucleotide down regulates the expression of ICAM-1, thereby decreasing RSV biding to ICAM-1.

3. The method according to claim 2, wherein said administration step further includes administering the composition to airway epithelial cells.

4. A method of treating RSV infection by administering an effective amount of the composition of claim 2 to a patient, wherein the antisense oligonucleotide down regulates the expression of ICAM-1.

5. The composition of claim 1, wherein said antisense oligonucleotide is complexed with a cationic lipid.

6. The composition of claim 1, wherein said composition further comprises an anti-ICAM-1 antibody.

7. The method according to claim 3, wherein the composition is administered intranasally to the airway epithelial cells.

8. The method according to claim 3, wherein the composition is administered orally to the airway epithelial cells.

9. The method according to claim 3, wherein the antisense oligonucleotide is complexed with a cationic lipid.

10. The method according to claim 3, wherein the composition further comprises an anti-ICAM-1 antibody.

11. The method according to claim 4, wherein said administration step further includes administering the composition to airway epithelial cells.

12. The method according to claim 11, wherein the composition is administered intranasally to the airway epithelial cells.

13. The method according to claim 11, wherein the composition is administered orally to the airway epithelial cells.

14. The method according to claim 4, wherein the antisense oligonucleotide is complexed with a cationic lipid.

15. The method according to claim 4, wherein the composition further comprises an anti-ICAM-1 antibody.

* * * * *

UNITED STATES PATENT AND TRADEMARK OFFICE
CERTIFICATE OF CORRECTION

PATENT NO.    : 6,900,299 B1  
DATED         : May 31, 2005  
INVENTOR(S)   : Shyam S. Mohapatra et al.

Page 1 of 1

It is certified that error appears in the above-identified patent and that said Letters Patent is hereby corrected as shown below:

Column 6,  
Line 9, "Gilboa et ai" should read -- Gilboa et al. --.

Column 10,  
Line 15, "Random printed" should read -- Random primed --.

Column 15,  
Line 61, "Schedi" should read -- Schedl --.

Column 16,  
Line 50, "and it" should read -- and its --.

Column 18,  
Line 53, "O. Cohn," should read -- D. Cohn, --.  
Line 65, "crystals" should read -- crystal --.

Signed and Sealed this

Twenty-third Day of August, 2005

JON W. DUDAS  
*Director of the United States Patent and Trademark Office*

SEQUENCE LISTING

<160> NUMBER OF SEQ ID NOS: 12

<210> SEQ ID NO 1
<211> LENGTH: 33
<212> TYPE: DNA
<213> ORGANISM: Artificial sequence
<220> FEATURE:
<221> NAME/KEY: Artificial sequence
<222> LOCATION: (1)..(33)
<223> OTHER INFORMATION: Primer

<400> SEQUENCE: 1
cctggcgaat tccagacatc tgtgtccccc tca                                33

<210> SEQ ID NO 2
<211> LENGTH: 24
<212> TYPE: DNA
<213> ORGANISM: Artificial sequence
<220> FEATURE:
<221> NAME/KEY: Artificial sequence
<222> LOCATION: (1)..(24)
<223> OTHER INFORMATION: reverse primer for ICAM-1

<400> SEQUENCE: 2
gtgtggatcc actgccacca atat                                         24

<210> SEQ ID NO 3
<211> LENGTH: 32
<212> TYPE: DNA
<213> ORGANISM: Artificial sequence
<220> FEATURE:
<221> NAME/KEY: Artificial sequence
<222> LOCATION: (1)..(32)
<223> OTHER INFORMATION: Forward primer for F gene

<400> SEQUENCE: 3
caagaattca tggagttgct aatcctcaaa ca                                32

<210> SEQ ID NO 4
<211> LENGTH: 36
<212> TYPE: DNA
<213> ORGANISM: Artificial sequence
<220> FEATURE:
<221> NAME/KEY: Artificial sequence
<222> LOCATION: (1)..(36)
<223> OTHER INFORMATION: Reverse primer for F gene

<400> SEQUENCE: 4
ctatgtcgac ttagttacta aatgcaatat tattta                            36

<210> SEQ ID NO 5
<211> LENGTH: 33
<212> TYPE: DNA
<213> ORGANISM: Artificial sequence
<220> FEATURE:
<221> NAME/KEY: Artificial sequence
<222> LOCATION: (1)..(33)
<223> OTHER INFORMATION: Forward primer for G gene

<400> SEQUENCE: 5
aatgaattca tgtccaaaaa caaggaccaa cgc                               33

<210> SEQ ID NO 6
<211> LENGTH: 30
<212> TYPE: DNA
<213> ORGANISM: Artificial sequence

```
<220> FEATURE:
<221> NAME/KEY: Artificial sequence
<222> LOCATION: (1)..(30)
<223> OTHER INFORMATION: Reverse primer for G gene

<400> SEQUENCE: 6
gttgtcgact aactactggc gtggtgtgtt                                              30

<210> SEQ ID NO 7
<211> LENGTH: 22
<212> TYPE: DNA
<213> ORGANISM: Artificial sequence
<220> FEATURE:
<221> NAME/KEY: Artificial sequence
<222> LOCATION: (1)..(22)
<223> OTHER INFORMATION: Forward primer for RSV-N

<400> SEQUENCE: 7
gcgatgtcta ggttaggaag aa                                                      22

<210> SEQ ID NO 8
<211> LENGTH: 24
<212> TYPE: DNA
<213> ORGANISM: Artificial sequence
<220> FEATURE:
<221> NAME/KEY: Artificial sequence
<222> LOCATION: (1)..(24)
<223> OTHER INFORMATION: Reverse primer for RSV-N

<400> SEQUENCE: 8
gctatgtcct tgggtagtaa gcct                                                    24

<210> SEQ ID NO 9
<211> LENGTH: 18
<212> TYPE: DNA
<213> ORGANISM: Artificial sequence
<220> FEATURE:
<221> NAME/KEY: Artificial sequence
<222> LOCATION: (1)..(18)
<223> OTHER INFORMATION: Forward primer for ICAM-1

<400> SEQUENCE: 9
atggctccca gcagcccc                                                           18

<210> SEQ ID NO 10
<211> LENGTH: 18
<212> TYPE: DNA
<213> ORGANISM: Artificial sequence
<220> FEATURE:
<221> NAME/KEY: Artificial sequence
<222> LOCATION: (1)..(18)
<223> OTHER INFORMATION: Reverse primer for ICAM-1

<400> SEQUENCE: 10
cacctggcag cgtagggt                                                           18

<210> SEQ ID NO 11
<211> LENGTH: 18
<212> TYPE: DNA
<213> ORGANISM: Artificial sequence
<220> FEATURE:
<221> NAME/KEY: Artificial sequence
<222> LOCATION: (1)..(18)
<223> OTHER INFORMATION: Forward primer for Beta-actin

<400> SEQUENCE: 11
cgcgagaaga tgacccag                                                           18
```

```
<210> SEQ ID NO 12
<211> LENGTH: 19
<212> TYPE: DNA
<213> ORGANISM: Artificial sequence
<220> FEATURE:
<221> NAME/KEY: Artificial sequence
<222> LOCATION: (1)..(19)
<223> OTHER INFORMATION: primer

<400> SEQUENCE: 12
atcacgatgc cagtcgtac                                                   19
```